(12) United States Patent
Klein et al.

(10) Patent No.: US 6,933,103 B1
(45) Date of Patent: Aug. 23, 2005

(54) BIOCOMPATIBLE TISSUE FOR THERAPEUTIC USE AND METHOD OF MAKING SAME

(75) Inventors: Dean Klein, North Oaks, MN (US); Leo D. Katzner, Shakopee, MN (US)

(73) Assignees: Brennen Medical, Inc., St. Paul, MN (US); Carbon Medical Technologies, Inc., St. Paul, MN (US)

( * ) Notice: Subject to any disclaimer, the term of this patent is extended or adjusted under 35 U.S.C. 154(b) by 532 days.

(21) Appl. No.: 10/086,933

(22) Filed: Mar. 1, 2002

Related U.S. Application Data

(63) Continuation of application No. 09/814,339, filed on Mar. 21, 2001, now abandoned.

(51) Int. Cl.[7] ............................ A61K 35/36; A61L 2/18
(52) U.S. Cl. ..................... 435/1.2; 435/1.1; 435/1.3; 424/572; 424/543
(58) Field of Search ................................ 424/543, 572; 435/1.1, 1.2, 1.3

(56) References Cited

U.S. PATENT DOCUMENTS 5,756,678 A * 5/1998 Shenoy et al. .............. 530/356

* cited by examiner

*Primary Examiner*—Jean C. Witz
(74) *Attorney, Agent, or Firm*—Moore, Hanson & Sumner, PLLP

(57) ABSTRACT

A biocompatible graft material and a method for making the same are disclosed. The method of making the graft material involves freezing and subsequently thawing a donated tissue sample in a bleach solution. The tissue is then washed in a detergent solution, treated with antimicrobial agents, and soaked in a hypertonic solution. The tissue is thereafter treated with sodium hydroxide and later hydrogen peroxide to yield the desired biocompatible graft material.

24 Claims, 1 Drawing Sheet

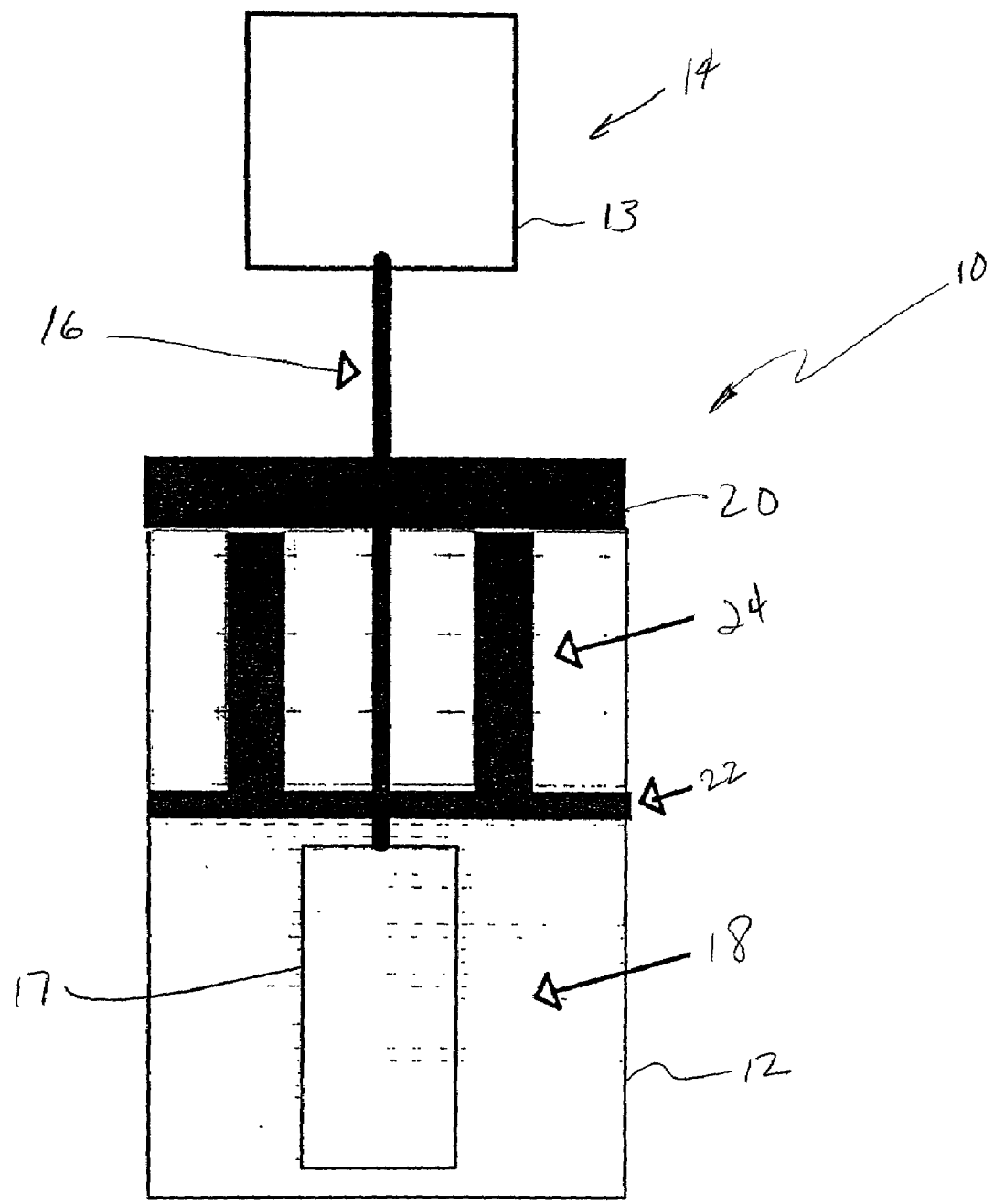

BIOCOMPATIBLE TISSUE FOR THERAPEUTIC USE AND METHOD OF MAKING SAME

This is a continuation of application Ser. No. 09/814,339 filed Mar. 21, 2001, now abandoned.

FIELD OF THE INVENTION

The present invention relates to a biocompatible graft material and a method for making the same. More specifically, the method of the present invention produces a substantially immunologically inert, non-toxic, non-allergenic, non-irritating, non-mutigenic, and non-hemolytic extra cellular matrix suitable for use as a graft material.

BACKGROUND OF THE INVENTION

In treating many illnesses and injuries, it is often useful to replace damaged or injured tissues with a biocompatible graft material. Examples of such graft materials are diverse and include, but are not limited to: coronary grafts, such as arteries, veins, and valves; structural tissues, such as ligaments and tendons, dura matter, and skin. The suitable graft materials may also be used for surgical procedures such as slings for the treatment of urinary incontinence, bulking agents for cosmetic or reconstructive surgery, heart valve replacements, pericardium repairs, arterial transplants, and surgical meshes for the repair of hernias, abdominal wall reconstructions, and pelvic floor reconstructions. Suitable graft materials may be derived from allogenic or exogenic sources. Furthermore, allogenic graft materials may further be derived from autologous or homologous sources and may even include cadaveric sources.

The use of biocompatible grafts is an important and sometimes indispensible part of a course of treatment. However, in order to avoid dangerously adverse reactions in a patient being treated with a biocompatible graft, it is first necessary to treat a freshly harvested graft material before it may be used as intended. This is particularly true where graft materials are derived from exogenic and homologous sources. Typically autologous sources of graft material represent a much lower risk with regard to adverse reactions but treatment may still be desired for the graft material to further reduce the likelihood of such reactions.

In its most basic form freshly harvested graft materials are treated to remove any type of reactive material that may be present in the graft material, such as antigens, viruses and prions. Once such reactive material is removed, the graft may be emplaced. Removal of reactive cellular materials leaves behind the structural component of the graft alone. The structural component of a graft is an extra cellular matrix comprised of collagen fibers that are by themselves typically biochemically inert. The failure to remove reactive cellular material from the extra cellular matrix can cause severe reactions to the graft material that can extend healing time or even result in the complete rejection of the graft material itself.

Much work has been done in the field of decellularizing the graft material to yield an essentially inert extra cellular matrix useful as a graft material. Typically, the collagenic extra cellular matrix of a freshly harvested graft material is cross-linked using an aldehyde such as formaldehyde or glutaraldehyde. Subsequent to this crosslinking step, the cross-linked extra cellular matrix of the graft material is subjected to an enzymatic process whereby cellular material present in the extra cellular matrix is lysed or otherwise removed. While these methods have produced useful biocompatible graphic materials, these methods are fairly complex and expensive. A need therefore exists for a method of producing a biocompatible graft material that is simple, efficient, and inexpensive.

These and other objectives and advantages of the invention will appear more fully from the following description, made in conjunction with the accompanying drawings wherein like reference characters refer to the same or similar parts throughout the several views.

BRIEF SUMMARY OF THE INVENTION

A preferred embodiment of preparing an immunologically inert graft material essentially comprises the steps of freezing and subsequently thawing a preselected quantity of body tissue in a bleach solution; washing the body tissue in a detergent solution; treating the body tissue with one or more anti-microbial and anti-viral solutions; soaking the body tissue in a hypertonic solution; soaking the body tissue in a solution comprising a caustic reagent; treating the body tissue with a hydrogen peroxide solution; and conserving the body tissue in a sterile environment.

More specifically the method of the present invention may comprise the steps of procuring body tissues from one of an autologous, heterologous or allogenic source; freezing the body tissues in a first bleach solution for a predetermined time and at a predetermined temperature; thawing the body tissues in a second bleach solution; rinsing the body tissues in water to remove bleach from the tissues; washing the body tissues in a detergent solution; rinsing the body tissue to remove the detergent solution; trimming the body tissue to a desired physical form; soaking the body tissue in an iodophor solution; rinsing the body tissue to remove the iodophor solution; soaking the body tissue in a hypertonic solution; rinsing the body tissue to remove the hypertonic solution therefrom; agitating the body tissue in a caustic solution; rinsing the body tissue in water under agitation to remove the caustic solution therefrom; treating the body tissue with a hydrogen peroxide solution under agitation; rinsing the body tissue in sterile water; and conserving the body tissues in a sterile environment until needed. It is believed that the graft material produced by the method of the present invention is itself a desirable item and therefore a graft material produced according the present invention is also claimed.

In the step of soaking the body tissue in the hypertonic and hypotonic solutions, it is preferred to use a simple saline solution as the hypertonic solution and water as the hypotonic solution. Additional steps that may be used in treating the body tissue with the hypertonic solution may include soaking the body tissue in a series of increasingly hypertonic solutions and rinsing the body tissue after each soaking in the hypotonic solution to remove the hypertonic solution therefrom. Preferably, the series of hypertonic solutions comprise 2%, 4%, 6%, 8%, 10% and 12% concentrations of a saline solution, respectively.

Preferably the caustic solution used to treat the body tissue comprises a sodium hydroxide solution. Specifically, it has been found efficacious to utilize a sodium hydroxide solution having a concentration of between 0.75 and 1.25 N. Alternatives to the sodium hydroxide solution include potassium hydroxide, ammonium hydroxide, calcium hydroxide, sodium dodecylsulfate, urea, phenol, and formic acid.

The treatment of the graft material with hydrogen peroxide is preferably done in a reaction chamber. A suitable reaction chamber comprises a receptacle portion into which hydrogen peroxide and the body tissue are placed and an agitator that is supported upon an axle within the receptacle. The agitator rotates so as to agitate the hydrogen peroxide and body tissue. A perforated cover is placed over the receptacle so as to maintain the body tissue below the surface of the hydrogen peroxide. Note that the hydrogen peroxide solution may be replaced with one of peracetic acid, perbenzoic acid, benzoyl peroxide, sodium peroxide, and potassium permanganate.

Anti-microbial solutions suitable for the purpose of reducing the bioburden level present in the extracellular matrix may comprise an iodophor or a bleach. More specifically, it is envisioned that the anti-bacterial solution may comprise one of povidone-iodine, sodium hypochlorite, and calcium hypochlorite. Note that it may also be desirable to substitute bleach for the iodophor or vice versa. Preferably the bleach used in treating the graft material will be sodium hypochlorite or calcium hypochlorite and the iodophor will be povidone-iodine.

It may also be desirable to treat the extracellular matrix with an antibiotic solution. One example of a suitable solution is kanamycin.

DESCRIPTION OF THE DRAWINGS

FIG. 1 is a schematic view of a hydrogen peroxide reaction chamber.

DETAILED DESCRIPTION OF THE INVENTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

As indicated above, graft materials produced by the method of the present invention may be used for surgical procedures such as slings for treatment for urinary incontinence, surgical meshes for repair of hernias, bulking agents for cosmetic or reconstructive surgery, abdominal wall reconstructions, pelvic floor reconstructions, heart valve replacements, pericardium repairs, or arterial transplants.

While the method of the present invention may be utilized to produce immunilogical inert graft material from tissues such as the arteries, heart valves, bone, or other organs and tissues of human or animal donors, preferred embodiments of the invention relates to the treatment of porcine skin for use as a sling material, a graft for pelvic floor reconstruction and as a skin replacement for treating skin-loss injuries such as burns and abrasions. The process of the present invention essentially comprises the steps of isolating and treating the derma layers of porcine skin, lysing non-collagenic cell material by treating the porcine skin with hypertonic and hypotonic saline solutions, altering proteins and non-collagenic tissue by treating the graft material with sodium hydroxide and hydrogen peroxide, and preparing the graft material for storage and/or use.

In the practice of the preferred embodiment of the present invention, suitable porcine hides are procured and after an initial washing, soaked for 30–45 minutes in an approximate 0.15 sodium hypochlorite bleach solution for the purpose of destroying bacteria and viruses. The hides are then frozen. While this freezing step does help to burst cells within the extra cellular matrix, it is essentially one of convenience and can be omitted if so desired. It is, however, necessary to soak the porcine hides in a bleach or equivalent solution to reduce the level of antigens present in the hides.

The frozen porcine hides are next placed in a 0.1–0.2% sodium hypochloride bleach solution and thawed therein for approximately 12 to 16 hours. The thawed porcine hides are then rinsed in water for up to 2 hours. While sterilized water may be used, it is preferred to use tap water at this juncture. The rinsed hides are then cut into stripes of a suitable size. Suitable alternatives to sodium hypochlorite that may be used in the first, procurement step and in the freezing and thawing steps include iodophor solutions such as povidone-iodine and calcium hypochlorite.

The rinsed strips of porcine skin are next placed in a detergent solution to remove fats and greases therefrom. This detergent solution may also remove the cellular membrane and proteins by disrupting lipids. Bleach may also be added to the detergent solution for the purposes of destroying bacteria and viruses. The strips are preferably soaked in the aforementioned detergent solution for approximately one half hour. After soaking in the detergent solution, the porcine skin strips are shaved to remove exterior hair shafts.

The porcine skin strips are next rinsed in purified or tap water for approximately two hours. During this rinsing step, the epidermis and dermis are removed from the hide using a dermatome. Using the dermatome, approximately 0.040 inches of the epidermis and dermis are removed from the porcine skin strips. This thickness may vary upon the desired final thickness of the graft material.

The strips of porcine skin are next transferred to a first iodophor solution (7.5% povidone-iodine) and allowed to soak therein for approximately 2 hours. Preferably, the porcine skin strips will be removed temporarily from the iodophor scrub solution so that additional hair stubble may be removed as by shaving. When the porcine skin strips have been soaked for a sufficient amount of time in the first iodophor scrub solution the skin is then rinsed in tap water and transferred to another iodophor solution (10% povidone-iodine) for approximately one half hour to further reduce the bioburden level of non-collagenic cellular materials present in the porcine skin samples. After this second iodophor solution soak, the porcine skin strips are again rinsed in purified or tap water, this time for approximately 3 hours. After rinsing, the porcine skin strips are trimmed to their final dimensions. In an alternate embodiment of this step, the porcine skin may be treated with a bleach solution containing sodium hypochlorite or calcium hypochlorite.

The portions of porcine skin are next measured and sorted into batches of known surface area. Each batch of porcine skin may optionally be next treated with an antibiotic solution to remove unwanted bacteria. The respective batches of porcine skin are treated with a concentration of an antibiotic solution of approximately 2000 milliliters for every 5 square feet of porcine skin. The preferred antibiotic solution contains 0.05% kanamycin sulfate in a 0.9% saline solution.

After treatment with antibiotics, the respective batches of porcine skin are then soaked alternately in increasingly hypertonic and hypotonic solutions for 2-hour intervals. The hypertonic solutions in this series comprise 2%, 4%, 6%, 8%, 10% and 12% sodium chloride in purified water. The hypotonic solution is purified water. Each treatment consists of a 2-hour soak without agitation. Therefore, this step in the production of an immunologically inert graft material requires 12 two-hour treatments for a total of approximately 24 hours. For example, a batch of porcine skin is placed in the hypertonic 2% saline solution for two hours. Thereafter this batch of porcine skin is placed in the hypotonic purified water for two hours and then into a hypertonic 4% saline solution for two hours. This process continues through the 12% saline solution. The treatment of the porcine skin batch with alternating hypertonic and hypotonic solutions acts to rupture cellular membranes by creating an osmotic pressure gradient across the cellular membranes. The cyclic nature of raising and lowering osmotic pressures using hypertonic and hypotonic solutions has been found very effective in lysing the cells present in the extra cellular matrix. Gradually increasing the concentration of the hypertonic solutions is a preferred means of increasing this lysing action. Note that the concentrations of the hypertonic solutions are not limited to the series listed above. Therefore, the hypertonic solutions may also comprise 1%, 3%, 5%, 7%, 9%, and 11% solutions and other series of increasingly concentrated solutions. Note that any ionic aqueous solution that is compatible with the intended use of the porcine skin will be suitable for use as a hypertonic solution in this treatment. Similarly, any non-ionic aqueous solution that is compatible with the intended use of the porcine skin will be suitable for use as a hypotonic solution in this treatment.

Following the last hypotonic solution rinse, the porcine skin is then placed in a 1 N (1 Normal) sodium hydroxide solution for approximately one hour. The porcine skin is agitated during this soaking step with a paddle mixer of known type running at approximately 120 rotations per minute. This step removes the epidermis from the extra cellular matrix and the majority of any remaining hair stubble that may be entrapped in the pores of the porcine skin. After the porcine skin has been soaked for its allotted time in the sodium hydroxide solution, the porcine skin is then placed in a quantity of purified water and agitated using a paddle mixer running at approximately 120 rotations per minute. This purified water rinse is essentially a polishing step that is a continuation of the sodium hydroxide treatment of the previous step due to the carryover of hydroxide ions from that previous step. Typically the pH of the purified water will rise and become highly caustic but less caustic than the first sodium hydroxide solution. This slightly lower pH is less destructive to the collagen of the porcine skin's extra cellular matrix, but will continue to remove non-collagenic cellular material from the extra cellular matrix. Alternate embodiments of this step may involve treating the porcine skin with potassium hydroxide, ammonium hydroxide, calcium hydroxide, sodium dodecylsulfate, urea, phenol, or formic acid. Note that not all of the alternate embodiments listed above are caustic chemicals. However, these chemicals are considered to be functional equivalents of sodium hydroxide in this step.

Upon removal from the purified water bath the porcine skin is soaked in a 3% solution of hydrogen peroxide for approximately two hours. The treatment of the porcine skin with the hydrogen peroxide acts to destroy non-collagenus material and also bleaches the porcine skin to a white to off-white color. Preferably this step will be performed under agitation in a hydrogen peroxide reaction chamber as illustrated in FIG. 1. The reaction chamber 10 of FIG. 1 comprises a container 12 that can hold a suitable quantity of hydrogen peroxide solution as well as the porcine skin that is to be treated therein. Because this hydrogen peroxide treatment is to be conducted under agitation, a paddle mixer 14 comprising a motor 13 having a shaft 16 extending therefrom and a paddle 17 affixed to the distal end of the shaft 16 is coupled to a cover 20 of the container 12 in a known manner. The hydrogen peroxide solution 18 disposed within the container will foam considerably upon the addition of the porcine skin that is to be treated therein. Therefore, to maintain the porcine skin within the hydrogen peroxide solution 18, a perforated plate 22 is inserted into the container 12 to slightly below the surface of the hydrogen peroxide solution 18 within the container 12. The perforated plate 22 has a shape such that the perimeter of the plate 22 is in close contact with the inside of the container 12 around substantially the entire perimeter of the perforated plate 22. In this manner, porcine skin placed in the hydrogen peroxide solution will remain entirely within the hydrogen peroxide solution 18 during treatment. The foam produced by the hydrogen peroxide will escape through the perforations formed through the plate 22 and will pass into the headspace 24 of the container 12. Alternate embodiments of this step may include treating the porcine skin with a solution comprising one of peracetic acid, perbenzoic acid, benzoyl peroxide, sodium peroxide, and potassium permanganate.

Upon removal from the reaction chamber 18, the porcine skin is rinsed in sterile water for approximately 1 hour. This rinsing step may be carried out multiple times. This rinsing step removes pyrogens and hydrogen peroxide carryover from the extracellular matrix of the porcine skin. At this stage the porcine skin has had substantially all of the non-collagenic cellular material removed from the extra cellular matrix thereof.

The porcine skin is then soaked in a 0.9% saline solution for approximately half an hour to stabilize the porcine skin and make it isotonic with respect to a recipient of the graft. The porcine skin is now an immunologically inert graft material that is ready for implantation.

Preferably the porcine graft material will be packaged, labeled and sterilized and conserved for future use. One alternative to standard packaging and sterilization is to freeze dry the porcine graft material.

As indicated above, a graft material produced according to the method of the present invention comprises a collagenic extra cellular matrix from which substantially all of the bioreactive cellular material has been removed. According to tests performed on samples of a porcine graft material produced using the method of the present invention, the resulting graft material is histopathologically acceptable in that an intramuscular implantation test showed complete incorporation of the graft material into the surrounding tissue. Additional testing involving the sensitization of the test subject by intradermal injection of porcine serum showed no erythema, no edema and no induration at 0.5, 1, 24, 48 and 72 hours after injection of the serum. Further testing revealed that a porcine graft material produced according to the method of the present invention did not cause adverse systemic reactions, was non-toxic, is a Grade I weak sensitizer, and was non-irritating, non-mutagenic, and non-hemolytic.

The invention described above may be embodied in other forms without departing from the spirit or essential characteristics thereof. The embodiments disclosed in this application are to be considered in all respects as illustrative and not restrictive. The scope of the invention is indicated by the appended claims rather than by the foregoing description and all changes which come within the meaning and range of equivalency of the claims are intended to be embraced therein.

What is claimed is:

1. A method of preparing an immunologically inert collagenic graft material comprising the steps of:
   procuring body tissue from one of an autulugous, heterologous or allogenic source;

soaking the body tissue in a bleach solution;

rinsing the body tissue in water to remove bleach solution from the tissues;

washing the body tissue in a detergent solution;

rinsing the body tissue to remove the detergent solution;

trimming the body tissue to a desired physical form;

soaking the body tissue in an iodophor solution;

rinsing the body tissue to remove the iodophor solution;

soaking the body tissue in a hypertonic solution;

rinsing the body tissue to remove the hypertonic solution therefrom;

agitating the body tissue in a caustic solution;

rinsing the body tissue in water under agitation to remove the caustic solution therefrom;

treating the body tissue with a peroxide solution under agitation;

rinsing the body tissue in sterile water; and conserving the body tissue in a sterile environment until needed.

2. The method of preparing a graft material of claim 1 wherein the hypertonic solution is a saline solution.

3. The method of preparing a graft material of claim 1 wherein the step of soaking the body tissue in a hypertonic solution further comprises the steps of:

soaking the body tissue in a series of increasingly hypertonic solutions and rinsing the body tissue after each soaking in a hypotonic solution to remove the hypertonic solution therefrom.

4. The method of preparing a graft material of claim 1 wherein the caustic solution comprises one of sodium hydroxide, potassium hydroxide, ammonium hydroxide, calcium hydroxide, sodium dodecylsulfate, urea, phenol, and formic acid.

5. The method of preparing a graft material of claim 1 wherein the caustic solution comprises a sodium hydroxide solution having a concentration of between 0.75 N and 1.25N.

6. The method of preparing a graft of material of claim 3 wherein the series of hypertonic solutions comprise 2%, 4%, 6%, 8%, 10% and 12% saline solutions.

7. The method of preparing a graft material of claim 1 wherein the body tissue is immersed in hydrogen peroxide in a reaction chamber comprising:

a receptacle portion into which hydrogen peroxide and the body tissue are placed;

an agitation that is supported upon an axle with in the receptacle and which rotates so as to agitate the hydrogen peroxide and body tissue; and a perforated cover placed over the receptacle so as to maintain the body tissue below the surface of the hydrogen peroxide.

8. A method of preparing an immunologically inert collagenic graft material comprising the steps of:

procuring body tissue from one of an autulugous, heterologous or allogenic source;

washing the body tissue in a detergent solution;

treating the body tissue with at least one anti-microbial and/or anti-viral solution;

soaking the body tissue in a hypertonic solution;

soaking the body tissue in a solution comprising a caustic reagent;

treating the body tissue with a hydrogen peroxide solution; and conserving the body tissue in a sterile environment.

9. A method of preparing an implantable collagenic graft material by removing cellular components from a preexisting extracellular matrix comprising the steps of:

freezing and subsequently thawing an untreated portion of the extracellular matrix in a bleach solution;

washing the extracellular matrix in a detergent solution;

lysing cellular components present in the extracellular matrix by soaking the extracellular matrix in a hypedonic solution;

soaking the extracellular matrix in a solution of sodium hydroxide; and soaking the extracellular matrix in a solution of hydrogen peroxide.

10. The method of preparing an implantable graft material of claim 9 further comprising the step of treating the extracellular matrix with an antibacterial agent.

11. The method of preparing an implantable graft material of claim 9 further comprising the step of soaking the extra cellular material in an iodophor solution.

12. The method of preparing an implantable graft material of claim 9 further comprising the step of treating the extracellular matrix with an antibiotic solution.

13. The method of preparing an implantable graft material of claim 9 further comprising the step of treating the extracellular matrix with an antibiotic solution comprising kanamycin.

14. The method of preparing a graft material of claim 1 wherein the body tissue is additionally treated with a bactericidal agent.

15. The method of preparing a graft material of claim 1 wherein the hydrogen peroxide solution may be replaced by one of peracetic acid, perbenzoic acid, benzoyl peroxide, sodium peroxide, or potassium permanganate.

16. The method of preparing an immunologically inert graft material of claim 8 wherein the anti-bacterial solution comprises one of an iodophor or a bleach.

17. The method of preparing an immunologically inert graft material of claim 8 wherein the anti-microbial and/or anti-viral solution comprises one of povidone-iodine, sodium hypochlorite, or calcium hypochlorite.

18. The method of preparing an immunologically inert graft material of claim 9 wherein one of potassium hydroxide, ammonium hydroxide, calcium hydroxide, sodium dodecylsulfate, urea, phenol, or formic acid may be substituted for sodium hydroxide.

19. The method of preparing an immunologically inert graft material of claim 8 wherein one of peracetic acid benzoyl peroxide, sodium peroxide, or potassium permanganate may be substituted for hydrogen peroxide.

20. The method of preparing an immunologically inert graft material of claim 8 wherein the bleach solution may comprise one of sodium hypochlorite or calcium hypochlorite.

21. The method of preparing an immunologically inert graft material of claim 9 wherein an iodophor may be substituted for the bleach solution.

22. The method of preparing an immunologically inert graft material of claim 21 wherein the iodophor comprises povidone-iodine.

23. The method of preparing an immunologically inert graft material of claim 1 further comprising the steps of initially freezing the body tissues in a first bleach solution for a predetermined time and at a predetermined temperature and then thawing the body tissues in a second bleach solution.

24. The method of preparing an immunologically inert graft material of claim 8 further comprising the step of freezing, and subsequently thawing a preselected quantity of body tissue in a bleach solution.

* * * * *

UNITED STATES PATENT AND TRADEMARK OFFICE
CERTIFICATE OF CORRECTION

PATENT NO. : 6,933,103 B1
DATED : August 23, 2005
INVENTOR(S) : Dean Klien and Leo D. Katzner It is certified that error appears in the above-identified patent and that said Letters Patent is hereby corrected as shown below:

Column 7,
Line 33, delete "and" and insert -- or --.
Line 37, delete "1.25N" and insert -- 1.25 N --.

Column 8,
Lines 57 and 59, delete "tissue" and insert -- tissues --.

Signed and Sealed this

Eighteenth Day of October, 2005

JON W. DUDAS
*Director of the United States Patent and Trademark Office*